US00PP27979P3

(12) United States Plant Patent
Stefanini

(10) Patent No.: US PP27,979 P3
(45) Date of Patent: May 9, 2017

(54) GRAPEVINE NAMED 'IASMA ECO 3'

(50) Latin Name: ***Vitisvinifera* L.**
Varietal Denomination: IASMA ECO 3

(71) Applicant: FONDAZIONE EDMUND MACH-CENTRO RICERCA ED INNOVAZIONE, San Michele All'Adige (TN) (IT)

(72) Inventor: Marco Stefanini, Bolzano (IT)

(73) Assignee: FONDAZIONE EDMUND MACH-CENTRO RICERCA ED INNOVAZIONE, San Michele All'Adige (IT)

( * ) Notice: Subject to any disclaimer, the term of this patent is extended or adjusted under 35 U.S.C. 154(b) by 19 days.

(21) Appl. No.: 13/999,224

(22) Filed: Jan. 31, 2014

(65) Prior Publication Data

US 2015/0223383 P1 Aug. 6, 2015

(51) Int. Cl.
*A01H 5/08* (2006.01)

(52) U.S. Cl.
USPC ..... Plt./205

(58) Field of Classification Search
USPC ..... Plt./205, 206, 207
See application file for complete search history.

(56) References Cited

U.S. PATENT DOCUMENTS

PP20,377 P2 * 10/2009 Cain ..... Plt./205

* cited by examiner

*Primary Examiner* — Susan McCormick Ewoldt
(74) *Attorney, Agent, or Firm* — Oblon, McClelland, Maier & Neustadt, L.L.P.

(57) ABSTRACT

This invention is a new and distinct grapevine variety named "IASMA ECO 3" which is characterized by producing white berries which mature 1 week earlier than the parents, and is much less sensitive to *Botrytis cinerea* compared to the parents. The present variety berries exhibit a loose bunch and have the presence of both geraniol and linalool.

3 Drawing Sheets

Latin name of the genus and species claimed: *Vitis vinifera* L.

Variety denomination: 'IASMA ECO 3'.

CROSS REFERENCE TO RELATED APPLICATIONS

The present application is related to Community Plant Variety application 2012/2344, filed in the Community Plant Variety Office on Oct. 25, 2012, the entire contents of which are hereby incorporated by reference.

BACKGROUND OF THE INVENTION

Discussion of the Background

The new and distinct grapevine described and claimed herein originated from a hand pollinated cross of Malvasia (Bianca) di Candia Aromatica (pollen parent) and Moscato Ottonel (seed parent), neither of which are protected by plant patent, plant variety protection certificate, or similar. The seeds were subsequently germinated and the resulting plants were planted in the field. The present variety of grapevine was selected as a single plant, and asexually propagated by hardwood cuttings. The resulting propagules were planted and were found to reproduce true-to-type through at least three generations of asexual reproduction, with the observations taking place from 2004 to 2010 in San Michele All'Adige(TN)—Trentino Alto Adige—Italy (46° 11' Lat. N, 11° 28' Long. E, 235 s.l.m.).

SUMMARY OF THE INVENTION

To the inventor's knowledge, there are no varieties similar to the new variety; being a crossing result, they contain 50% of the genetic material of the seed parent and 50% of the genetic material of the pollen parent.

The present variety produces white berries in the parents. The present variety matures 1 week earlier than the parents, and is much less sensitive to *Botrytis cinerea* compared to the parents. The present variety berries exhibit a loose bunch and have the presence of both geraniol and linalool.

The variety IASMA ECO 3 has no anthocyanin pigmentation of tips, while in Muscat Ottonel variety the anthocyanin pigmentation is very strong and widespread and in Malvasia di Candia variety is weak and piping.

The shoot on blooming is horizontal in Muscat Ottonel variety, semi erect in Malvasia di Candia variety and in the variety IASMA ECO 3.

The dorsal and ventral shoot on Blooming in Muscat Ottonel variety and Malvasia di Candia variety, in internodes and nodes, is green (150A) with red (44B) strips, while it is green (150A) in the variety IASMA ECO 3.

The variety IASMA ECO 3 tendrils are long, like those of Malvasia di Candia variety, while in Muscat Ottonel variety they are medium.

The Young leaf of the variety IASMA ECO 3 is bronze (N25A), becoming green (149B), while that of Malvasia is green (150A) and red (44B), and that of Moscato Ottonel being reddish (44b). The variety IASMA ECO 3 has no prostrate and erect hairs on the ribs and between the ribs, while the Malvasia di Candia variety has medium density creeping hairs between the ribs and on the ribs. Erect hairs are absent. In Muscat Ottonel variety there are no erect hairs on the ribs.

The mature leaf (UPOV 17) is small in the variety IASMA ECO 3, medium sized in Muscat Ottonel, and large in Malvasia di Candia. The color of the upper side is green (150 A) in Muscat Ottonel and dark green (134N) in Malvasia di Candia, and medium green (149A) in the variety IASMA ECO 3.

The goffering of blade and undulation of blade between main and lateral veins are absent in Malvasia di Candia variety and Muscat Ottonel variety, and weak in the variety IASMA ECO 3.

The variety IASMA ECO 3 teeth are convex; their size, in relation to blade size, is medium and the length of teeth is long compared to their width. Muscat Ottonel variety teeth are convex in both sides, their size in relation to blade size is short and the length of teeth compared with their width is short. In Malvasia di Candia variety teeth are rectilinear in both sides, and their size in relation to blade size is medium, the length of teeth compared with their width is medium.

The petiole sinus of the variety IASMA ECO 3 is slightly open and the shape of its base is V shaped, while in Muscat Ottonel variety is closed V shaped and in Malvasia di Candia variety is slightly open and U shaped.

The base of upper lateral sinuses is U shaped in the variety IASMA ECO 3, and brace shaped in Muscat Ottonel variety and V shaped in Malvasia di Candia variety.

The density of erect hairs on the veins of the lower side is high in the variety IASMA ECO 3, absent in Malvasia di Candia variety and medium in Muscat Ottonel variety. Erect hairs are present in Muscat Ottonel variety on the main veins of the upper side, in Malvasia di Candia variety and the variety IASMA ECO 3 are absent. The length of petiole, compared to that of middle vein, is slightly shorter in the variety IASMA ECO 3 and longer in Malvasia di Candia variety and equal in Muscat Ottonel variety.

The main color of woody shoot is reddish brown in Moscato Ottonel variety and brownish in Malvasia di Candia variety and in the variety IASMA ECO 3.

In the variety IASMA ECO 3, the first inflorescence stand on 2nd node, and has very high basal bud fertility, in Malvasia di Candia variety the insertion of the first inflorescence is at 3 and 4 node, and has medium fertility of the buds; Muscat Ottonel variety first inflorescence is at the third internode for and has 3 very low basal fertility. The number of inflorescences per shoot is 1.1 to 2 in parents, and 2.1 to 2.5 in the variety IASMA ECO 3. The first inflorescence of the variety IASMA ECO 3 is about 13 cm long, the date of full bloom is around 5th June, while in Muscat Ottonel variety the date of full bloom is 7th June, and its first inflorescence is 20 cm long. The Malvasia di Candia variety first inflorescence is 15 cm and the date of full bloom is 7th June.

The variety IASMA ECO 3 bunch is >16 cm long, >8 cm wide, medium dense, the length of the peduncle is medium, with lignification only at the base, with conical shape and absence of wings. In Muscat Ottonel variety the bunch is less than 16 cm long, 8-12 cm wide, dense, and the length of the peduncle is short, with medium lignification, with conical shape and absence of wings. In Malvasia di Candia variety the bunch is very long (>24 cm), >20 cm wide, loose, the peduncle is long, the peduncle is lignified, the bunch shape is conical-cylindrical with and 1-2 wings.

The berry length is medium in the variety IASMA ECO 3 and Muscat Ottonel variety, small in Malvasia di Candia variety, the berry width is short in Muscat Ottonel variety and Malvasia di Candia variety and medium in the variety IASMA ECO 3.

The berry color in the variety IASMA ECO 3 and Muscat Ottonel variety is green yellow (1C), the color of Malvasia di Candia variety berry is yellow (7C) with hilum visible. The variety IASMA ECO 3 hilum is barely visible.

The variety IASMA ECO 3 foliage (size) is semi-erect. The variety IASMA ECO 3 has a slightly short petiole, compared to middle vein, with no hairs. The young flower color is bronze (N25A). The variety IASMA ECO 3 sexual organs are fully developed stamens and fully developed gynoecium. The fruit flesh color is yellow-green (149D). The crop time is similar to the parent varieties (15 days after Chardonnay).

DETAILED DESCRIPTION OF THE INVENTION

Figure 1:
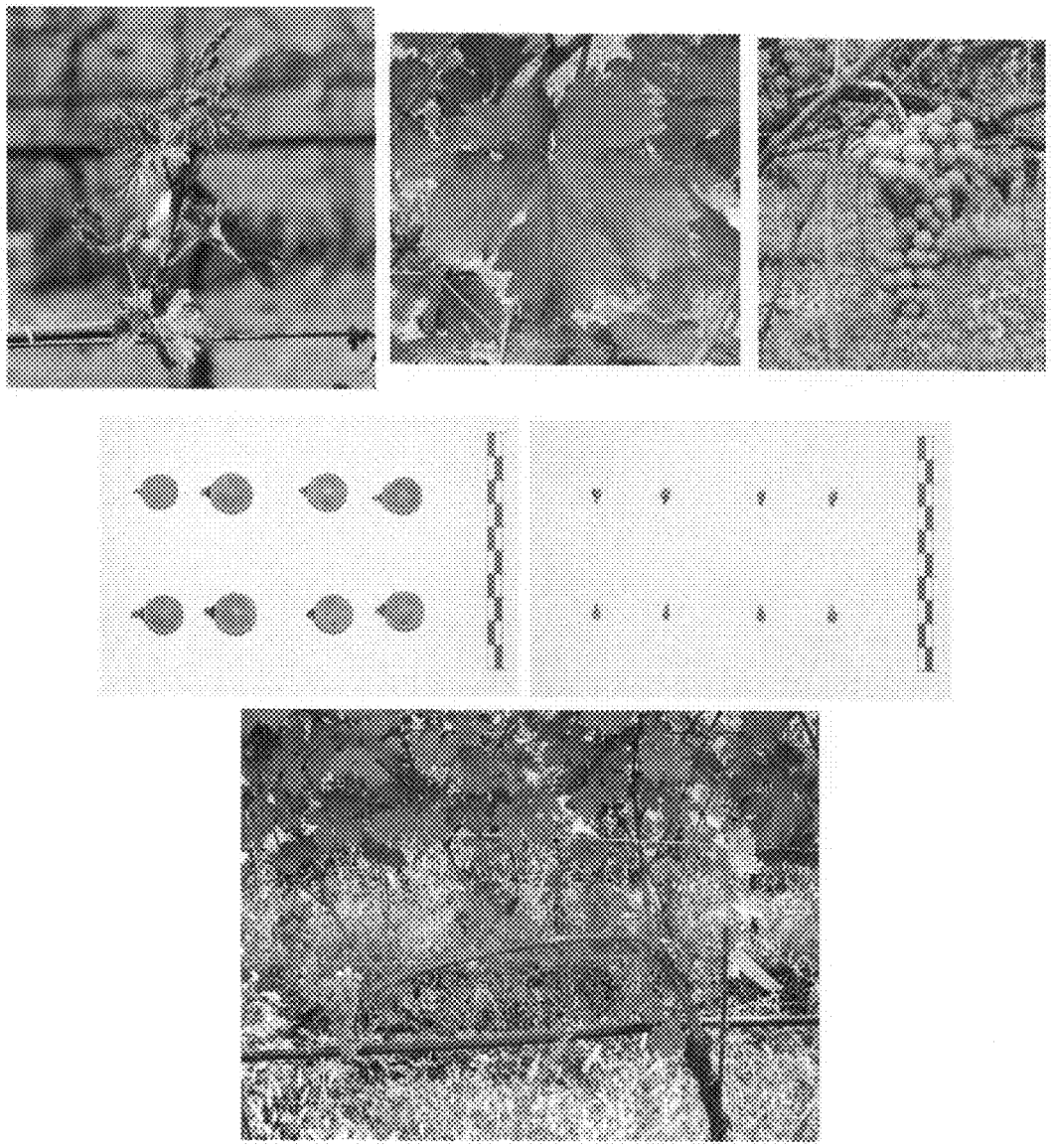
FIG. 1 provides photographic illustration in full color of the variety IASMA ECO 3 in various views. The colors are as nearly true as is reasonably possible in a color representation of this type.
Figure 2:
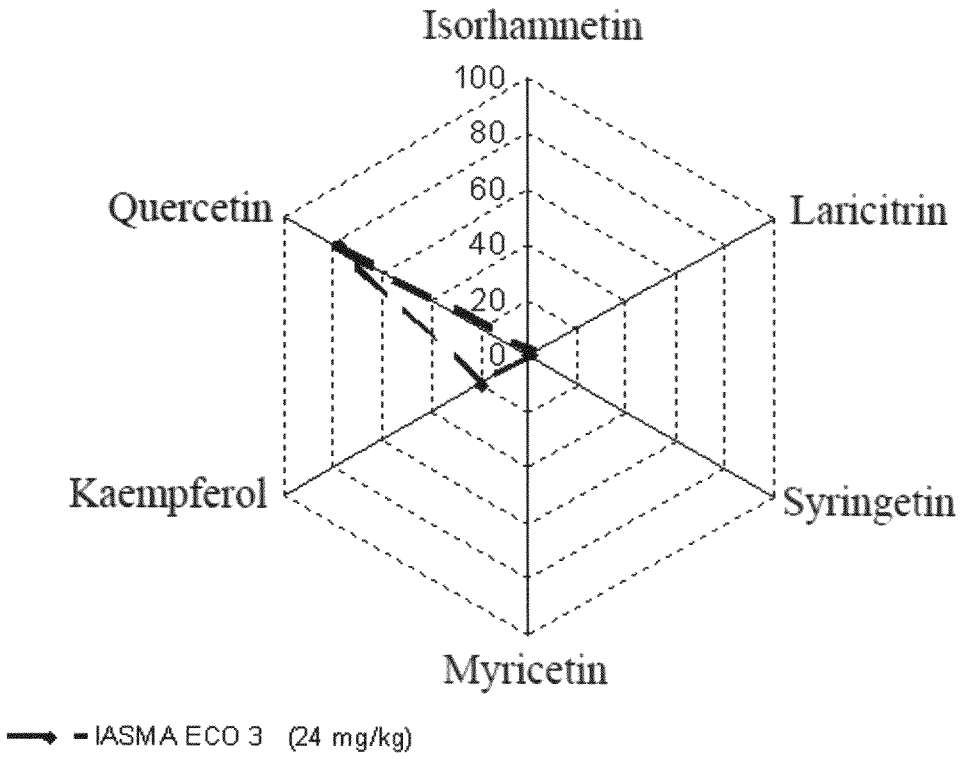
FIG. 2 provides a graphical representation of the average profile of a glycone flavonols in the present invention variety by percentile.
Figure 3:
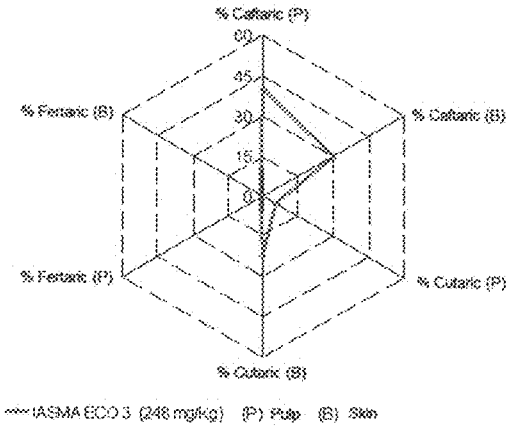
FIG. 3 provides a graphical representation of the average profile of cinnamic acids in the present invention variety by percentile and by mg/kg.
Figure 3:
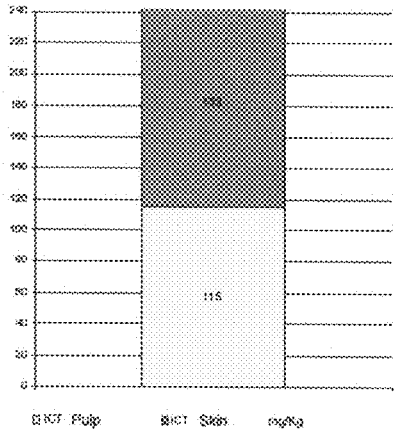

Throughout this specification, color names beginning with a small letter signify that the name of that color, as used in common speech, is aptly descriptive.

Throughout this specification subjective description values conform to those set forth by the Community Plant Variety Office (France) in the Technical Questionnaire for Grapevine varieties. Color names beginning with a capital letter or represented as a numerical designator indicate values based upon R.H.S. Colour Chart, published by The Royal Horticultural Society, London, England.

The descriptive matter which follows pertains to 'IASMA ECO 3' plants grown in the vicinity of San Michele All'Adige (TN)—Trentino Alto Adige—Italy (46° 11'Lat. N, 11° 28' Long. E, 235 s.l.m.) from 2004 to 2010, and is believed to apply to plants of the variety grown under similar conditions of soil and climate elsewhere:

Young shoot: 10-30 cm.

*Aperture of tip.*—Fully open.

*Distribution of anthocyanin pigmentation of tip.*—Absent.

*Intensity anthocyanin pigmentation of tip.*—None.

*Density prostrate hairs of tip.*—None.

*Density erect hairs of extremity.*—None.

Shoot on blooming:

*Attitude.*—Semi-erect.

*Color of dorsal side of internodes.*—Green, 150A.

*Color of ventral side of internodes.*—Green, 150A.

*Color of dorsal side of nodes.*—Green, 150A.

*Color of ventral side of nodes.*—Green, 150A.

*Density erect hairs on nodes.*—None.

*Density erect hairs on internodes.*—None.

*Density prostrate hairs on nodes.*—None.

*Density prostrate hairs on internodes.*—None.

*Anthocyanin pigmentation on the latent bud scales.*—Absent.
*Intensity anthocyanin pigmentation bud scales.*—None.

Tendrils:
*Number of consecutive tendrils.*—2 or less.
*Length.*—Long.

Young leaf:
*Color of the upper side.*—Green (149B) with bronze (N25A) strips.
*Density prostrate hairs between the veins.*—None.
*Density erect hairs between the veins.*—None.
*Density prostrate hairs on veins.*—None.
*Density erect hairs on veins.*—None.

Mature leaf:
*Size of blade.*—Small.
*Shape of blade.*—Pentagonal.
*Number of lobes.*—Five.
*Color of the upper side.*—Medium green, 149A.
*Anthocyanin pigmentation veins on the upper side.*—Absent.
*Anthocyanin pigmentation veins on the lower side.*—Absent.
*Goffering of blade.*—Weak.
*Undulation of blade between main and lateral veins.*—Present.
*Profile in cross section.*—Revolute.
*Blistering of upper side.*—Weak.
*Shape of teeth.*—Convex.
*Size of teeth in relation to blade size.*—Medium.
*Length of teeth compared with their width.*—Long.
*Degree of opening of petiole sinus.*—Little open.
*Shape of base of petiole sinus.*—V-shaped.
*Teeth of the petiole sinus.*—Absent.
*Petiole sinus base delimited by veins.*—Absent.
*Degree of opening of upper lateral sinuses.*—Slightly overlapped.
*Shape of base of upper lateral sinuses.*—{-shaped.
*Teeth in the upper lateral sinuses.*—Absent.
*Density of prostrate hairs between the veins of the lower side.*—Absent.
*Density of erect hairs between the veins of the lower side.*—Absent.
*Density of prostrate hairs on the veins of the side.*—None.
*Density of erect hairs on the veins of the lower side.*—High.
*Prostrate hairs on the main veins of the upper side.*—Absent.
*Erect hairs on the main veins of the upper side.*—Absent.
*Density of prostrate hairs on petiole.*—None.
*Density of erect hairs on petiole.*—None.
*Length of petiole compared to middle vein.*—Slightly shorter.

Woody shoot:
*Cross section.*—Elliptic.
*Structure of surface.*—Striate.
*Main color.*—Brownish.

Inflorescence:
*Sexual organs.*—Stamens complete, gynoecium developed.
*Inflorescence; insertion of 1st inflorescence.*—Up to the 2nd node.
*Inflorescence; number of inflorescences per shoot.*—2.1 to 2.5 inflorescences.
*Shoot; fertility of basal buds.*—Buds 1-3 very high.
*Length of 1st inflorescence.*—Long — approximately 13 cm.
*Date of full bloom.*—Early June.
*Time of bloom.*—Medium as compared with similar varieties in the area of S. Michele all'Adige — TN.

Bunch:
*Length.*—Medium, <16 cm.
*Width.*—Narrow, <8 cm.
*Density.*—Medium.
*Length of peduncle.*—Medium.
*Lignification of peduncle.*—At the base only.
*Shape.*—Conical.
*Number of wings.*—Absent.

Berry:
*Length.*—Medium, <18 mm.
*Width.*—Medium, <18 mm.
*Uniformity of size.*—Uniform.
*Shape.*—Globose; roundish.
*Color of the skin.*—Green yellow (1C).
*Uniformity of the color of the skin.*—Uniform.
*Bloom.*—Medium.
*Thickness of the skin.*—Medium.
*Hilum.*—Little visible.
*Intensity anthocyanin pigmentation of the flesh.*—None.
*Juiciness of the flesh.*—Medium juicy.
*Must yield.*—Low.
*Firmness of the flesh.*—Slightly firm.
*Particular flavor.*—Muscat.
*Length of pedicel.*—Short, <7 mm.
*Ease of detachment from pedicel.*—Medium.
*Formation of seeds.*—Complete.
*Time of autumn coloring of leaves.*—Yellow, 3A.

Phenologic characteristics:
*Time of bud burst.*—Medium (comparable to the parent varieties); 3 days after Chardonnay.
*Time of full bloom.*—Medium (comparable to the parent varieties); 7 days after Chardonnay.
*Time of berry ripening.*—Medium (5).
*Time of maturity.*—Medium (comparable to the parent varieties). 15 days after Chardonnay.

Productive characteristics:
*Real fertility of the buds.*—1.45.
*Potential fertility.*—1.62.
*Position of the first bunch.*—2nd-3rd bud.
*Production of grapes per vine.*—Kg 2.25.
*Yield per hectare quintal.*—96.
*Medium weight bunch.*—g 189.
*Medium weight berry.*—g 2.10.
*Sugars, brix degree.*—22.52.
*Total acid content.*—g/l 5.82.
*pH.*—3.46.

The present variety tested negative against each of the GFLV, ArMV, GLRaV-1, GLRaV-3, and GVA viruses.

Findings of Molecular Investigations

DNA was extracted from young leaves of different accessions for each variety by using the Doyle and Doyle extraction method (1990) as modified by Grando et al. (2003). Molecular markers were obtained by analyzing DNA specimens at the 9 microsatellite loci specified by the European projects named Gen-Res81 and Grape-Gen06 for vine variety characterisation and at locus VMC1B11 (*Vitis* Microsatellite Consortium). In particular, the primers and amplification conditions described by Thomas and Scott (1993) for locus VVS2, Bowers et al. (1996) for loci VVMD5 and VVMD7, Bowerset al. (1999) for loci VVMD25, VVMD27, VVMD28 and VVMD32 and Sefc et al. (1999) for loci VrZAG62 and VrZAG79 were applied. PCR products were separated and analyzed with the Genetic Analyzer ABI3130 and the GeneMapper® v4.0 software. The results are shown in Table 1 below.

TABLE 1

| Microsatellite markers | | | | | | | | |
|---|---|---|---|---|---|---|---|---|
| 'IASMA | VVMD5 | | VVMD7 | | VVMD25 | | VMD27 | |
| ECO 3' | 225 | 227 | 233 | 239 | 250 | 256 | 177 | 187 |
| 'IASMA | VVMD28 | | | VVMD32 | | | VVS2 | |
| ECO 3' | 249 | | 259 | 241 | 265 | | 130 | 132 |
| 'IASMA | VMC1B11 | | | VrZAG62 | | | VrZAG79 | |
| ECO 3' | 185 | | 185 | 193 | 203 | | 255 | 259 |

Findings of Cultivation Tests

The series of summary tables below contain the findings for various vintage years concerning the variety IASMA ECO 3 vine compared to the reference vine variety. Average data relative to some plant production parameters observed at the San Michele a/A (TN) vineyard (vintage years 2004-2010): vine grown following the Guyot method (arched shoot pruned at 8-10 sprouts/vine). The results are shown in Table 2:

TABLE 2

| | 'IASMA ECO 3' S. Michele a/A | CHARDONNAY S. Michele a/A |
|---|---|---|
| Grape/vine production (kg) | 2.25 | 3.22 |
| Actual shoot fertility | 1.45 | 1.49 |
| Potential shoot fertility | 1.62 | 1.54 |
| Wood/vine production (kg) | 0.489 | 0.686 |
| Must sugars (°Brix) | 22.52 | 20.06 |
| Moulds (%) bunch botrytis | 5.3 | 7.5 |
| Moulds (%) rachis desiccation | 0.00 | 0.0 |
| Grape/wood ratio | 4.60 | 4.69 |

Average data relative to mechanical bunch analysis and must chemical composition. Collection of bunches in the vintage years 2004-2010 at technological maturity (first or second half of September). Vineyard in S. Michele a./A. (Girelli TN).

TABLE 3

| 'IASMA ECO 3' | | Values Average v. | Limit v. Min | Max |
|---|---|---|---|---|
| Mech. bunch analysis | | | | |
| bunch average weight | g | 189 | 158 | 323 |
| berry average weight | g | 2.10 | 1.85 | 2.60 |
| berry longitudinal diameter | mm | 18 | 14 | 22 |
| berry average diameter | mm | 17 | 12 | 19 |
| Bunch composition | | | | |
| berries | (% in weight) | 95.3 | 94.1 | 96.6 |
| stems | (% in weight) | 4.7 | 3.4 | 5.9 |

TABLE 3-continued

| 'IASMA ECO 3' | | Values Average v. | Limit v. Min | Max |
|---|---|---|---|---|
| Berry composition | | | | |
| skins | (% in weight) | 23.8 | 18.5 | 27.6 |
| seeds | (% in weight) | 4.2 | 2.9 | 5.8 |
| pulp and must | (% in weight) | 72.0 | 63.5 | 77.3 |
| must yield | (% volume/weight) | 68.4 | 60.5 | 71.1 |
| Must chemical composition | | | | |
| sugars | °Brix | 22.52 | 20.00 | 25.20 |
| total acidity | g/l | 5.82 | 4.43 | 6.98 |
| pH | | 3.46 | 3.25 | 3.95 |
| tartaric acid | g/l | 5.47 | 3.94 | 7.02 |
| malic acid | g/l | 2.08 | 1.44 | 3.02 |
| potassium | g/l | 1.46 | 1.11 | 2.32 |

Average data relative to the analysis of secondary metabolite profiles (aglycone flavonols, cinnamic acids and aromatic compounds of fruits) that characterize the variety's compositional phenotype.

Average profile of aromatic compounds in the free and complexed form are shown in Table 4:

| AROMATIC COMPOUNDS | | | | | | |
|---|---|---|---|---|---|---|
| | Oxide A | Oxide B | linalol | 4-ter-pineol | HO-trienol | Oxide C |
| IASMA ECO 3' (free) | 16 | 15 | 138 | <1 | 74 | 12 |
| IASMA ECO 3 (complexed) | 264 | 58 | 473 | <1 | 109 | 53 |
| | Oxide D | citronellol | Methyl salicylate | | nerol | geraniol |
| IASMA ECO 3' (free) | 85 | 22 | 1 | | <1 | 14 |
| IASMA ECO 3 (complexed) | 52 | 14 | 53 | | <1 | 186 |
| | benzyl alcohol | b-phenyl ethyl alcohol | HO-diol I | HO-diol II | hydroxy-citronellol | |
| IASMA ECO 3' (free) | 117 | 24 | 14 | 68 | 246 | |
| IASMA ECO 3 (complexed) | 557 | 102 | 118 | 18 | 24 | |
| | hydroxy-nerol | 8-hydroxy-linalol trans | 8-hydroxy-linalol cis | | 7-hydroxy-geraniol | |
| IASMA ECO 3' (free) | <1 | 15 | 25 | | 18 | |
| IASMA ECO 3 (complexed) | <1 | 232 | 171 | | 133 | |
| | Trans-geranic acid | phenol | rose oxide I | rose oxide II | benzal-dehyde | |
| IASMA ECO 3' (free) | 2 | 29 | <1 | <1 | <1 | |
| IASMA ECO 3 (complexed) | 30 | 906 | <1 | <1 | <1 | |
| | 3-hoxy-O-ionol | damascone | hexanol | 3-hexanol trans | 3-hexanol cis | |
| IASMA ECO 3' (free) | 10 | <1 | 88 | <1 | 47 | |

-continued

| AROMATIC COMPOUNDS | | | | | |
|---|---|---|---|---|---|
| IASMA ECO 3 (complexed) | 78 | <1 | 12 | <1 | 16 |

Values expressed as μg/Kg of n-heptanol standard grape RF = 1

According to the average profile of aromatic compounds in the free and complexed form, this variety can be classified as an aromatic variety.

Wine analysis.

Origin of grape: Vineyard in S. Michele a./A. (Girelli TN) Vintage years 2004-2010.

TABLE 5

| | Values | | |
|---|---|---|---|
| | Average | Limit v. | |
| 'IASMA ECO 3' | v. | Min | Max |
| alcohol content % vol. | 12.81 | 11.12 | 13.43 |
| total acidity in tartaric acid g/l | 4.91 | 3.75 | 5.15 |
| dry extract g/l | 20.60 | 17.38 | 22.50 |
| pH | 3.50 | 3.45 | 3.65 |
| catechins and proantocyanidins mg/1(+) catechin | 20 | 14 | 29 |
| total polyphenols mg/1(+) catechin | 212 | 148 | 264 |

Behaviour in Vegetative Multiplication

Grafted vine affinity with the most popular holders—good

Cultivation Characteristics and Suitability

The present invention vine variety shows good vigour with medium sprouting stage, with green-yellow, medium-sized, globose berry with medium thickness skin. The bunch is medium-sized, conical, relatively compact and often winged. It has a good yield and is relatively quite resistant to *botrytis*. Its physiological maturity occurs in the second stage; it shows a good capacity to accumulate sugars with low acidity values, especially in warm vintage years. It can perfectly stand winter cold and shows a good resistance to downy mildew and a medium resistance to powdery mildew. It prefers relatively fertile mixed hilly soils. It is ideal to produce delicate aromatic wines at altitudes exceeding 400 m above sea level or on slopes facing north.

Use

The present invention vine variety is particularly suited to produce fresh aromatic white wine; its taste recalls lemon balm and white peach with intense organoleptic characteristics; medium-low acidic strength (low in warm vintage years). It produces medium-body wines with good alcohol content and good sapidity, slightly aromatic and very peculiar. It can also be successfully used to produce still pure or mixed wines.

The invention claimed is:

1. A new and distinct variety of grapevine as herein illustrated and described.

* * * * *